United States Patent [19]

Venter et al.

[11] Patent Number: 5,183,930
[45] Date of Patent: Feb. 2, 1993

[54] TRANSESTERIFICATION CATALYST

[75] Inventors: Jeremia J. Venter, Telford; Christine McDade, North Wales, both of Pa.

[73] Assignee: Rohm and Haas Company, Philadelphia, Pa.

[21] Appl. No.: 899,791

[22] Filed: Jun. 17, 1992

[51] Int. Cl.$^5$ .............................................. C07C 67/02
[52] U.S. Cl. ..................................... 560/217; 560/234
[58] Field of Search ................................ 560/217, 234

[56] References Cited

U.S. PATENT DOCUMENTS

| | | | |
|---|---|---|---|
| 4,032,550 | 6/1977 | White et al. | 260/410.6 |
| 4,043,941 | 8/1977 | White et al. | 260/410.6 |
| 5,037,978 | 8/1991 | Mirabelli | 544/171 |
| 5,066,829 | 11/1991 | Fried et al. | 560/217 |

FOREIGN PATENT DOCUMENTS

| | | |
|---|---|---|
| 0745581 | 7/1970 | Belgium . |
| 0145588 | 6/1985 | European Pat. Off. . |
| 3105418 | 9/1978 | Japan . |
| 7206639 | 12/1982 | Japan . |
| 2-193944 | 7/1990 | Japan . |
| 0706397 | 12/1979 | U.S.S.R. . |
| 1016042 | 1/1966 | United Kingdom . |
| 1059875 | 2/1967 | United Kingdom . |
| 1184490 | 3/1970 | United Kingdom . |

*Primary Examiner*—Paul J. Killos
*Attorney, Agent, or Firm*—Terence P. Strobaugh

[57] ABSTRACT

A process is described for preparing carboxylic acid esters via transestierification using a new heterogeneous, transition-metal transesterification catalyst of enhanced activity. The catalyst is prepared by an improved method of reacting a metal alkoxide to form an active species and absorbing the metal containing species onto a support. The method requires the controlled hydrolysis of a transition metal alkoxide to prepare an oligomer, which is then absorbed onto a hydroxylic support.

9 Claims, No Drawings

TRANSESTERIFICATION CATALYST

BACKGROUND OF THE INVENTION

The present invention relates to supported transition metal transesterification catalysts. It also relates to a method for preparation of such catalysts.

Simple and polymeric esters are major products of the chemical industry. As such, there are a wide variety of processes for their production. These include direct esterification by reactions of alcohols with carboxylic acids or anhydrides as well as various interchange reactions including alcoholysis, in which the alcohol moiety of an ester is exchanged by another alcohol, acidolysis, in which the carboxylic acid moiety is exchanged by another carboxylic acid, and transesterification in which the alcohol moieties of two different esters exchange with each other. These interchange reactions will be collectively referred to as transesterification reactions.

In the absence of some type of catalyst, esterification and transesterification reactions tend to be quite slow. For this reason reactions are almost always catalyzed. Acids, bases, and transition metal based catalysts are all used in various applications. However, there are a number of problems associated with the use of acidic and basic catalysts. These catalysts often promote undesirable side reactions which can make it difficult to isolate a pure product without employing extensive purification procedures. Furthermore, they also often require neutralization at the end of the reaction as well as removal from the product. This again may entail extensive purification procedures.

To avoid many of the problems associated with acidic or basic catalysts, transition metal catalysts are gaining increased use. In addition to avoiding problems with neutralization associated with the acidic and basic catalysts, they are often more selective in their activity, thus avoiding unwanted side reactions. Transition metal catalysts can be roughly divided into two classes, homogeneous and heterogeneous. Homogeneous catalysts are soluble in the reaction medium. Because of this they suffer from one of the major problems of many acidic and basic catalysts. That is, removal of the catalyst at the end of the reaction is difficult, if not impossible. Often even trace amounts of transition metal impurities in products are intolerable and, therefore, complex steps are often needed to reduce transition metal content to acceptable levels. This results in additional processing steps, waste, and/or yield losses. Furthermore, homogeneous catalysts are often destroyed during removal. This "once through" utilization of the catalyst can result in unacceptably high manufacturing costs.

Heterogeneous catalysts are relatively insoluble in the reaction medium. As a result, they avoid many of the purification problems associated with acidic, basic, and homogeneous catalysts. Often they can be removed from the product by a simple filtration step. However, since their activity occurs at the catalyst surface, rather than in solution, heterogeneous catalysts tend to have low activity.

Thus, the goal of much catalyst research is to discover heterogeneous catalysts which are not only selective and easily removed from the reaction mixture, but are also highly active.

U.S. Pat. No. 4,043,941 (hereinafter '941) and U.S. Pat. No. 4,032,550 (hereinafter '550) describe the preparation of heterogeneous transesterification catalysts with high activity and good stability which are free-flowing powders. Preparation is accomplished by heating a solid hydroxylic support with a molar excess (based on support surface hydroxyl groups) of a transition metal alkoxide in an aliphatic hydrocarbon solvent in the presence of water. The transition metal alkoxide reacts with the surface hydroxyl groups and then is further hydrolzed by water resulting in a highly cross-linked matrix of transition metal atoms with bridging oxygen linkages. For activity, an excess of the transition metal over surface hydroxyl groups is required. This excess can be from 1:1 up to about $10^6:1$. Water is required for preparation of the catalyst; at least one mole for each bridging oxygen atom.

Although the procedure used in the '941 and '550 patents produces catalysts with what would be considered generally high activity, a need still exists for heterogeneous transesterification catalysts with even higher activity. Thus, an objective of this invention was to prepare heterogeneous transesterification catalysts with higher activities than currently available. A further objective was to prepare these catalysts using anhydrous support materials in the absence of water. A still further objective was to prepare esters via transesterification using the improved catalysts.

We have found that transesterification catalysts with unexpectedly high activity can be prepared by a unique modification of the catalyst preparation procedure used in '941 and '550. Rather than the one step process of '941 and '550, our invention requires two steps. In the first, a transition metal alkoxide is partially hydrolyzed to form an oligomer. This oligomer is then reacted with a hydroxylic support in the second step to form the heterogeneous catalyst. The advantages of the two step process will become apparent from the following disclosure.

DETAILED DESCRIPTION OF THE INVENTION

Transition metals useful in this invention are any from Groups IVb, Vb, and VIb of the Periodic Table of the Elements which form alkoxides of the general formula:

$$M(OR)_nQ_m$$

wherein M is the transition metal; OR is an alkoxy radical containing from 1 to 20 carbon atoms such as ethoxy, n-propoxy, isopropoxy, n-butoxy, isobutoxy, tert-butoxy, 2-ethylhexyloxy, allyloxy, n-decyloxy, tridecyloxy, stearyloxy, cyclopentyloxy, and the like; n is an integer from 2 to the valence number of the transition metal M; Q is an inert group with valence number r which will not react with hydroxyl groups of the support, the alkoxide radical OR, or the alcohol ROH formed therefrom; and m is an integer such that n+rm equals the valence number of the transition metal M. Saturated branched or straight-chain alkoxy radicals containing 2 to 8 carbons are preferred. Most preferred are n-butoxy radicals. Preferred transition metals include titanium, zirconium, hafnium and vanadium. Most preferred is titanium.

The hydroxylic support can be any commonly used support material having a hydroxylic surface, that is, which contains a plurality of hydroxyl groups on the matrix surface. The support can be either natural or synthetic. Examples include alumina, silica, fumed silica, silica gel, clays (such as kaolinite, montmorillonite, vermiculite, chlorite, and mica types), zeolites, zirconia, titania, thoria, megnesia, aluminates, carbon blacks, synthetic inorganic oxides of silicon, magnesium, aluminum, zinc, and their mixtures, and the like. In addition, organic polymers with pendant hydroxyl groups are also useful. Oxides of silicon and aluminum are preferred supports.

The transition metal oligomer is prepared by partial hydrolysis of the transition metal alkoxide with water to produce a networked polymer. The amount of water can be varied over a wide range depending on the extent of polymerization desired in the oligomer. One mole of water is required for each mole of oxygen bridges formed. Both branched and straight-chain oligomers are produced. The partial hydrolysis can be conducted in any organic solvent in which the transition metal alkoxide is soluble and stable. However, it is typically carried out in the alcohol corresponding to that of the transition metal alkoxide. Likewise, the water can be either pure or diluted with an organic solvent. Often it is diluted with the solvent used to dissolve the transition metal alkoxide. The water, or water solution, is usually, but not necessarily, added dropwise to the transition metal alkoxide solution. Temperature, pressure, and rate of addition are not critical. Following reaction, the solvent need not be removed. However, for the second step, if desired, the solvent can be removed and replaced with another solvent in which the oligomer is soluble.

The second step involves incorporation of the oligomer onto the catalyst support. The oligomer is first dissolved in a solvent. As above, the solvent is not critical so long as it is one in which the oligomer is soluble and stable. The oligomer solution is combined with the support. The support can either be dry or in a solvent slurry. Support particle size, surface area, and pore size are not critical. However, supports with high surface areas and larger pore sizes generally will result in catalysts with higher activity. Order of addition and the oligomer/support ratio are also not critical. Although the support need not be anhydrous, any free water present will react with the oligomer, increasing the number of oxygen bridges. For this reason it is preferably to dry the support prior to reaction. The procedure can produce catalysts containing preferably from about 1 weight percent to about 20 weight percent transition metal based on total catalyst weight. Most preferred catalysts contain from about 3 weight percent to about 12 weight percent transition metal.

One advantage of this invention is that because water is only necessary for preparation of the oligomer a variety of anhydrous support materials can be used. Those catalyst preparation procedures which require water for incorporation of the transition metal catalyst onto the support cannot maintain the anhydrous nature of the support. Another advantage of this invention is that the oligomer can be tailored to a desired composition and characterized prior to reaction with the support material.

Although the mechanism of improved catalyst properties which this invention provides is not fully understood, we believe that when the oligomer and the support surface react, multiple points of attachment result. This produces a monolayer of oligomer at the support surface in which, in the ideal case, every transition metal atom in the oligomer is attached to a surface hydroxyl group. This reduces the possibility of hydrolytic or alcoholic displacement of the transition metal, or its oligomer, from the support surface. By contrast, catalysts produced using existing technology (e.g. the '941 patent process), due to the large excess of transition metal atoms compared to the surface hydroxyl groups, up to $10^6$ to 1, consist of a number of long chains of oligomer branching from the support surface which can be displaced. Furthermore, a monolayer of catalyst on the support surface would be expected to result in a more active catalyst because every transition metal atom is available. With the excess of metal to surface hydroxyls of known catalysts, much of the catalyst itself is inaccessible to the reactants. This theory of the invention is presented here as a possible explanation for the surprising results obtained and in no way is intended to limit the scope of the invention.

The transesterification catalysts of this invention can be used to produce esters in continuous or in batch processes. In general, the catalysts are effective in transesterification reactions between any alcohol ($C_1$–$C_{30}$) and any ester or anhydride ($C_2$–$C_{30}$). Useful alcohols include, for example, ethanol, chloroethanol, cyanoethanol, n-propanol, sec-propanol, n-butanol, t-butanol, isoamyl alcohol, n-hexanol, 2-ethylhexanol, n-octanol, n-decanol, isodecanol, capryl alcohol, lauryl alcohol, myristyl alcohol, cetyl alcohol, stearyl alcohol, oleyl alcohol, tridecyl alcohol, cyclohexanol, benzyl alcohol, o-, m-, and p-methoxybenzyl alcohols, ethylene glycol, 1,2-propylene glycol, 1,3-propylene glycol, 1,2-butanediol, 1,3-butanediol, 1,4-butanediol, 1,4-pentanediol, 3-methyl-1,5-pentanediol, 2,3-dimethyl-2,3-butanediol, phenylethyl alcohol, triphenylethyl alcohol, trimethylol propane, mannitol, sorbitol, glycerol, pentaerythritol, 1,4-cyclohexanedimethanol, xylenol, bisphenols, diethylene glycol, triethylene glycol, polyoxyethylene or polyoxypropyleneglycols of molecular weight up to about 4,000, diethylene glycol monomethylether, diethylene glycol monoethylether, triethylene glycol monomethyl ether, butoxyethanol, butylene glycol monobutylether, dipentaerythritol, tetrapentaerythritol, diglycerol, triglycerol, and the like. Useful esters or anhydrides include, for example, acetic, phenylacetic, triphenylacetic, propionic, acrylic, methacrylic, β-phenylacrylic, n-butyric, isobutyric, valeric, isovaleric, 5-phenyl-n-valeric, hexanoic, 2-ethylhexanoic, heptanoic, caproic, octanoic, pelargonic, lauric, myristic, palmitic, stearic, oleic, erucic, linoleic, linolenic, eleostearic, lignoceric, malonic, succinic, glutaric, adipic, pimelic, azelaic, sebacic, decane-1,10-dicarboxylic, pentadecane-1,15-dicarboxylic, pentacosane-1,25-dicarboxylic, propane-1,2,3-tricarboxylic, crotonic, maleic, fumaric, mesaconic, citraconic, itaconic, muconic, aconitic, cyclopropane carboxylic, cyclobutane carboxylic, cyclohexane carboxylic, cyclopropane dicarboxylic, cyclohexane dicarboxylic, cyclohexane-1,2,3,4,5,6-hexacarboxylic, cyclopentene-2-carboxylic, cyclohexadiene-1,2-dicarboxylic benzoic, toluic, α-naphthoic, b-naphthoic, o-, m-, and p-ethylbenzoic, p-phenylbenzoic phthalic, isophthalic, terephthalic, trimellitic, pyromellitic, hydroxyacetic, chloracetic bromoacetic, cyanoacetic, lactic, α-, or b-hydroxypropionic, citric, ricinoleic, α-, or b-chloroacrylic, 2-hydroxycyclohexane carboxylic, o-, m-, or p-, chloro, bromo, nitro, or methoxybenzoic, hydroxyphthalic, tall oil fatty acids, lanolin fatty acids, coconut fatty acids, montan wax acids, polymeric acids, and the like.

Mole ratios of ester to alcohol can vary from 0.01 to 100. Reaction time may vary from as short as 1 hour to as long as 48 hours depending on the reactivity of the catalyst for the particular reaction mixture. The reaction can be conducted at any temperature. However, temperatures of between 50° C. and 200° C. have been found to yield sufficient reaction rates. Temperatures of between 90° C. and 110° C. are preferred. The catalyst to reactant ratio can also vary considerably, from 0.1 to 100 parts catalyst to 100 parts reactants by weight. However, 10 to 20 parts catalyst to 100 parts reactants by weight is preferred. For continuous reactions, the catalyst is added to the reactor of choice and contacted with the reactants. The contact time is varied by changes in the feed flow rate. Products and any remaining unreacted starting materials can be removed from the reactor either continuously or in batches. The catalyst can be easily removed from the products and starting materials by filtration.

EXAMPLES AND COMPARATIVE EXAMPLES

The following examples and comparative examples illustrate the present invention more specifically. The invention is in no way limited to these specific examples. The silicas used in these examples were CS-1022 and CS-2040 from PQ Corporation having the following properties:

|  | CS-1022 | CS-2040 |
| --- | --- | --- |
| Pore Volume, ml/gram | 1.5 | 2.2 |
| Pore Diameter, Å | 260 | 218 |
| Surface Area, m$^2$/gram | 229 | 416 |

EXAMPLE 1

Preparation of Titanium Catalyst on Silica Gel (0.2% Moisture)

Water (6.69 g., 372 mmole) and 6M hydrochloric acid (0.905 g., 24.8 mmole) were combined in approximately ten volumes of n-butanol in a constant addition funnel fitted to a flask containing tetra-n-butyltitanium (TBT, 83.7 g., 248 mmole) dissolved in an equal volume of n-butanol. The apparatus was maintained under a nitrogen atmosphere. The TBT/n-butanol mixture was constantly stirred. The water/n-butanol mixture was added dropwise (approximately 4 drops per minute) to the TBT/n-butanol mixture. After stirring for 24 hours, the solvent was removed under rotary evaporation to give a tannish, flaky solid (titanium oligomer). A portion of the oligomer (38 g.) was dissolved in cyclohexane (130 ml.). To this solution was added CS-2040 silica gel (42.5 g., 20-50 mesh, dried under vacuum at about 110° C. to give a moisture content of less than 0.2%). The mixture was shaken vigorously for one hour and then the solvent was removed under vacuum at ~50° C. The catalyst was dried for 64 hours under vacuum at ~120° C.

EXAMPLE 2

Preparation of Titanium Catalyst on Silica Gel (2% Moisture Level)

Example 2 was prepared using the procedure of Example 1 with water (7.75 g., 430 mmole), 6M hydrochloric acid (1.3 g., 35.9 mmole), and TBT (121.9 g., 359 mmole) used to make the TBT oligomer. The entire quantity of oligomer was dissolved in cyclohexane (110 ml.) and added to CS-1022 silica gel (125 g., dried to 2% moisture content). After shaking for 2 hr., the solvent was removed under vacuum at ~50° C. and the catalyst dried for 16 hr. under vacuum at ~140° C.

EXAMPLE 3

Preparation of Titanium Catalyst on Silica Gel (0.2% Moisture Level) Using Nozzle Mixing Water (23.2 g., 176 mmole)/6M hydrochloric acid (0.5 g., 14.7 mmole)/butanol and TBT (50 g., 147 mmole)/butanol mixtures were prepared as in Example 1. They were then combined in a mixing chamber outfitted with two small inlet nozzles and a larger outlet opening. The inlet nozzles were arranged to give intimate mixing of the inlet streams in the exact proportions of the final composition. The combined mixture was then stirred for 24 hr. The solvent was removed under vacuum at ~50° C. leaving a sticky solid TBT oligomer.

The oligomer was dissolved in cyclohexane (91 ml.) and CS-1022 silica gel (100.7 g, 0.2% Moisture Level) was added. After vigorous shaking for 2 hr., the solvent was removed under vacuum at ~50° C. The catalyst was dried under vacuum at ~140° C.

COMPARATIVE EXAMPLE 4

Preparation of Titanium Catalyst on Clay Using Tetraisopropyltitanium (TPT)

Example 4 was prepared using a procedure from the '550 patent by adding, over a period of 1.5 hr, a solution of tetraisopropyltitanium (TPT, 33.5 g.) in mineral oil (27.5 g.) to montmorillonite clay (10 g., containing approximately 4% moisture) in a three neck reaction flask outfitted with an addition funnel (containing the TPT/mineral oil solution), a reflux condenser and a thermometer. During the addition, the temperature was gradually increased to 120° C. Additional TPT (34 g.)/mineral oil (21 g.) solution was added dropwise while the temperature was gradually increased to 140° C. at which point isopropanol began distilling off. The mixture was then heated to 200° C. for 5 hr. This procedure produced greenish solid catalyst (35.6 g.).

COMPARATIVE EXAMPLE 5

Preparation of Titanium on Clay Catalyst Using TBT

Example 5 was prepared using the procedure for preparation of Example 4 except that TBT was used instead of TPT and n-butanol was distilled off at a temperature of 165° C. The procedure produced a dark green catalyst (40 g.).

EXAMPLE 6

Preparation of Titanium on Clay Catalyst

The oligomer for this example was prepared using the procedure of Example 1 from water (9.5 g.), 6M hydrochloric acid (1.1 g., 29.4 mmole) and TBT (100 g., 294 mmole). Also using the procedure of Example 1, the oligomer was dissolved in cyclohexane (200 ml.) and added to Montmorillonite clay (200 g., containing approximately 1% water). The procedure produced a lumpy catalyst which had to be ground to a fine powder for subsequent use.

EVALUATION OF CATALYST ACTIVITY

Catalyst activity was measured in the following manner:

Either butanol or lauryl alcohol (ROH) and methyl methacrylate (MMA) were premixed in a molar ratio of 1:2. An inhibitor (either, phenothiazine or the methyl ether of hydroquinone) was added and the mixture dehydrated by distillation of the MMA/water azeotrope using a 10 tray Oldershaw column fitted with a Mumberg overhead system set at 10% forward. Dehydration was considered complete when the distillate temperature rose above that expected for the azeotrope. The resulting mixture was stored and used as a stock solution.

The catalyst to be evaluated (typically 26 g.) and ROH/MMA stock solution (typically 260 g.) were combined in a 500 ml baffled flask attached to a Mumberg head set for 10% forward. The mixture was heated under vacuum with sparging by an 8% oxygen in nitrogen gas mixture. Conditions were adjusted such that the mixture was kept at 90° C. The concentration of methanol produced in the reaction was kept below 0.3% in the mixture by removal as a methanol/MMA azeotrope. During reaction, the mixture was sampled hourly to measure conversion rate, expressed as percent conversion of ROH to product ester. The reaction was allowed to proceed for six hours and then allowed to cool overnight under atmospheric pressure. The liquid was then decanted leaving the catalyst behind. This procedure was then repeated with the same catalyst four additional times to evaluate catalyst lifetime. The results of these evaluations are in Tables 1 and 2.

TABLE 1

Catalyst Evaluation for Formation of Lauryl Methacrylate

| Catalyst | % Conversion Run Number | | | | |
|---|---|---|---|---|---|
| | 1 | 2 | 3 | 4 | 5 |
| Example 2 | 69.0 | 790 | 74.0 | 73.0 | 66.0 |
| Example 3 | 38.0 | 59.0 | 45.0 | 36.0 | 34.0 |
| Comparative Example 4 | 6.8 | 8.1 | 6.6 | 5.2 | 4.0 |
| Comparative Example 5 | 6.5 | 10.5 | 20.5 | 11.2 | 5.1 |
| Example 6 | 14.3 | 13.1 | 4.4 | 2.9 | 2.5 |

TABLE 2

Catalyst Evaluation for Formation of Butyl Methacrylate

| Catalyst | % Conversion Run Number | | | | |
|---|---|---|---|---|---|
| | 1 | 2 | 3 | 4 | 5 |
| Example 1 | 57.0 | 74.0 | 91.0 | 96.0 | 99.0 |
| Comparative Example 5 | 3.0 | 8.1 | ~8.0 | 8.0 | 5.1 |
| Example 6 | 15.8 | ~13.0 | 12.2 | 8.6 | 5.4 |

RESULTS

The data in Tables 1 and 2 demonstrate that the catalysts of this invention (Examples 1,2,3, and 6) are significantly more active than similar catalysts prepared using existing technology (Comparative Examples 4 and 5). Examples 1,2, and 3 particularly show this advantage being almost an order of magnitude more active. Even the least active of the example catalysts of this invention (Example 6) is still more active that existing catalysts.

We claim:

1. A process for the batch, continuous or semicontinuous preparation of carboxylic acid esters by ester interchange of a carboxylic acid ester with another carboxylic acid ester, an alcohol, or a carboxylic acid comprising heating the reactants at a temperature of between 50° C. and 200° C. in the presence of a supported transition metal transesterification catalyst prepared by:

a. preforming an oligomer by reacting water with a transition metal alkoxide of the general formula:

$M(OR)_n Q_m$ 

wherein M is a transition metal; OR is an alkoxy radical wherein R is an alkyl group of from 1 to 20 carbon atoms, n is an integer from 2 to the valence number of the transition metal M; Q is a group with valence number r which will not react with hydroxyl groups of the support, the alkoxide radical OR, or the alcohol ROH formed therefrom; and m is an integer such that $n+rm$ equals the valence number of the transition metal M;

b. mixing a solution of the oligomer in an inert solvent with a solid substrate having a plurality of surface hydroxyl groups.

2. The process of claim 1 wherein the reactants are heated at a temperature of between 90° C. and 110° C.

3. The process of claim 1 wherein the transesterification catalyst is present at a concentration of from about 0.1 to about 100 parts by weight of catalyst to 100 parts by weight of reactants.

4. The process of claim 1 wherein the carboxylic acid ester produced is an acrylate ester or a methacrylate ester.

5. The process of claim 1 wherein the transition metal alkoxide R is a saturated branched- or straight-chain alkyl group containing 2 to 8 carbon atoms; Q is oxygen; m is zero or 1; and $n+2m$ equals the valence number of the transition metal M.

6. The process of claim 1 wherein m is zero and the transition metal M is selected from titanium, zirconium, hafnium, or vanadium.

7. The process of claim 1 wherein the solid substrate is selected from silica, alumina, or mixtures thereof.

8. The process of claim 1 wherein the transition metal alkoxide is a titanium tetraalkoxide.

9. The process of claim 1 wherein the solid support is selected from silica, alumina, or mixtures thereof.

* * * * *